(12) United States Patent
Kumiega et al.

(10) Patent No.: US 9,572,772 B2
(45) Date of Patent: *Feb. 21, 2017

(54) XYLITOL CONTAINING COMESTIBLE PRODUCT

(71) Applicant: The Hershey Company, Hershey, PA (US)

(72) Inventors: Steven M. Kumiega, Hummelstown, PA (US); Thomas J. Carroll, Mechanicsburg, PA (US); Ashley L. Boldt, Harrisburg, PA (US); Paula M. Gibson, Harrisburg, PA (US); Robert J. Huzinec, Hummelstown, PA (US); Burton Douglas Brown, Hershey, PA (US); David M. Stumpf, Palmyra, PA (US)

(73) Assignee: The Hershey Company, Hershey, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/868,471

(22) Filed: Sep. 29, 2015

(65) Prior Publication Data

US 2016/0015633 A1    Jan. 21, 2016

Related U.S. Application Data

(62) Division of application No. 13/392,689, filed as application No. PCT/US2010/047071 on Aug. 30, 2010, now Pat. No. 9,179,695.

(60) Provisional application No. 61/238,017, filed on Aug. 28, 2009.

(51) Int. Cl.
*A61K 8/00* (2006.01)
*A61K 9/00* (2006.01)
*A23G 3/34* (2006.01)
*A23G 3/42* (2006.01)
*A61K 9/14* (2006.01)
*A61K 31/616* (2006.01)
*A23G 3/38* (2006.01)
*A61K 47/10* (2006.01)
*A61K 47/18* (2006.01)

(52) U.S. Cl.
CPC ............ *A61K 9/0056* (2013.01); *A23G 3/0021* (2013.01); *A23G 3/38* (2013.01); *A23G 3/42* (2013.01); *A23L 27/34* (2016.08); *A23L 29/37* (2016.08); *A23P 10/25* (2016.08); *A23P 30/20* (2016.08); *A61K 9/145* (2013.01); *A61K 31/616* (2013.01); *A61K 47/10* (2013.01); *A61K 47/18* (2013.01); *A23V 2002/00* (2013.01)

(58) Field of Classification Search
CPC ...... A61K 9/0056; A61K 47/10; A61K 9/145; A61K 31/616; A23L 27/34; A23G 3/00
See application file for complete search history.

(56) References Cited

U.S. PATENT DOCUMENTS 5,045,325 A * 9/1991 Lesko ............... A23G 4/04
366/83

* cited by examiner

*Primary Examiner* — Snigdha Maewall
(74) *Attorney, Agent, or Firm* — Design IP

(57) ABSTRACT

The present invention relates to a process for preparing a comestible product comprising xylitol said method comprising: (a) subjecting a composition comprising xylitol in an amount ranging from about 60% to about 100% by weight to extrusion treatment inside an extrusion apparatus under conditions sufficient to form and maintain the xylitol in a slurry and (b) then shaping the extruded slurry and cooling the product to form a solid. The present invention additionally is directed to a product produced therefrom.

20 Claims, 9 Drawing Sheets

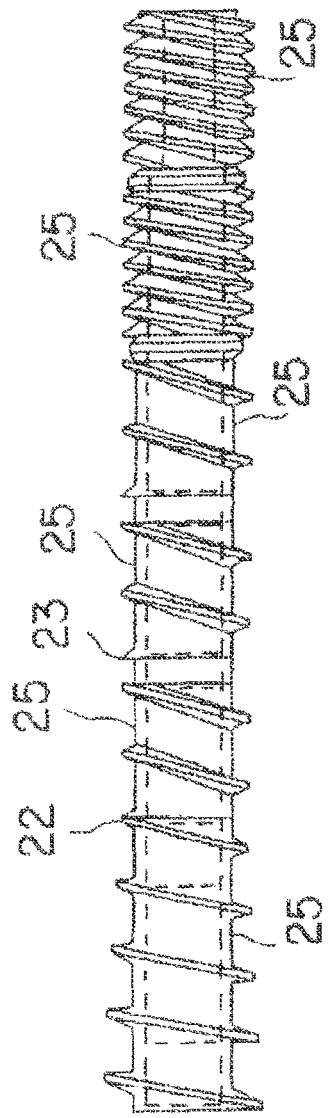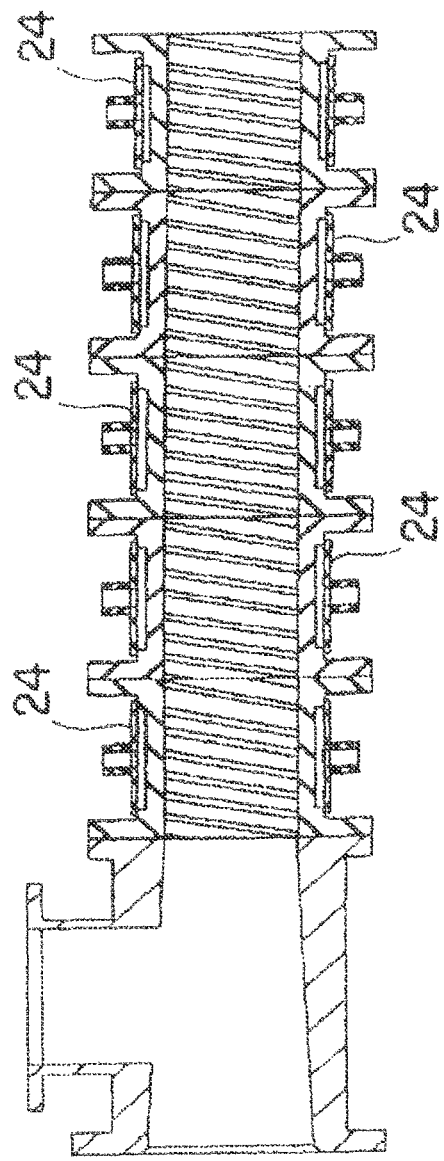

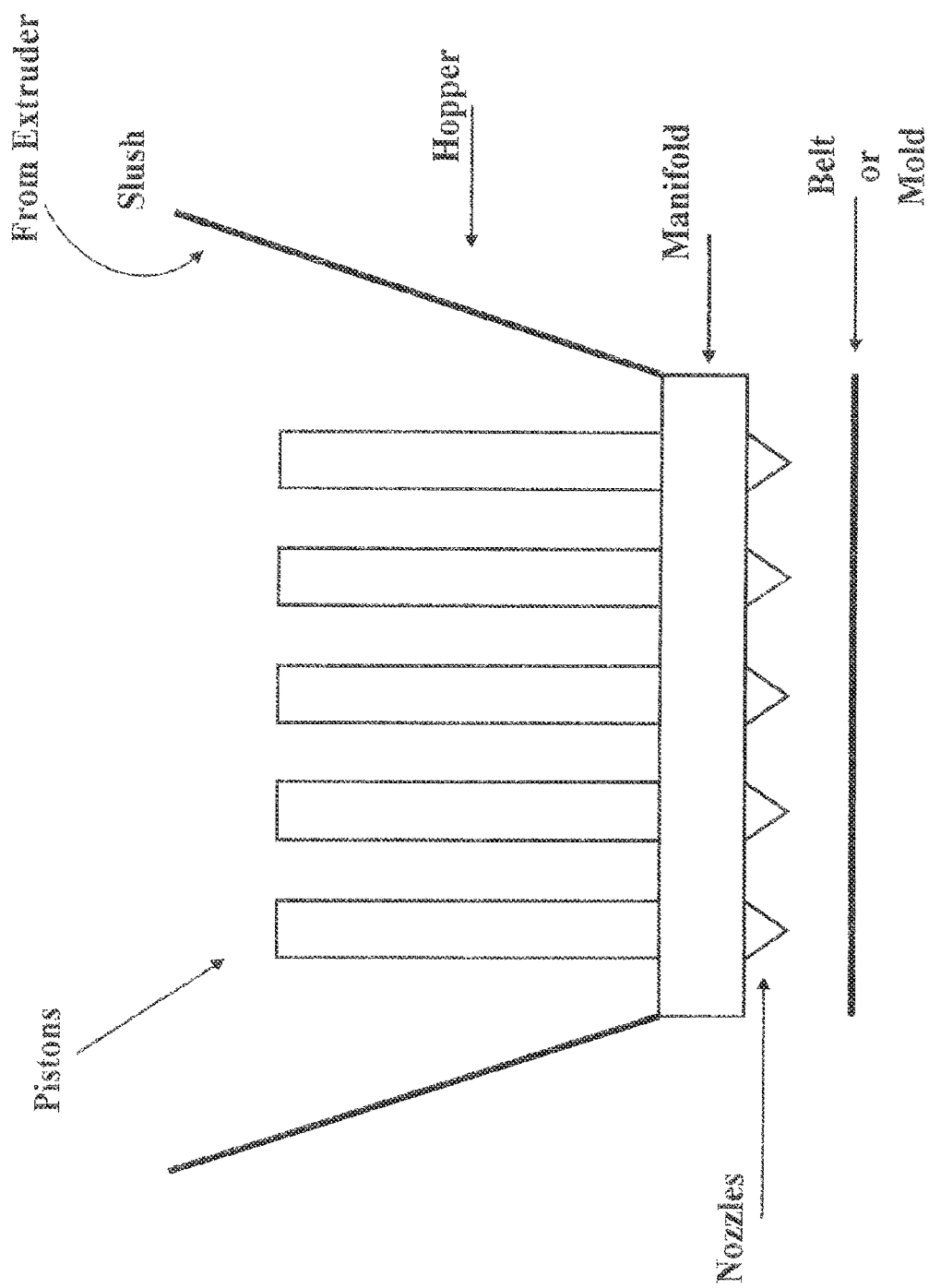

XYLITOL CONTAINING COMESTIBLE PRODUCT

FIELD OF THE INVENTION

The present invention relates to a process for the production of a non-compressible comestible product comprising xylitol and the comestible product comprising xylitol produced therefrom.

BACKGROUND OF THE INVENTION

Xylitol is a naturally occurring five carbon sugar alcohol. It occurs naturally in many fruits and vegetables and is produced by the human body during normal metabolism. It is a sweet crystalline product, white in color, odorless and soluble in water. In crystalline form, it quickly dissolves in the mouth. It has a negative heat of dissolution, and thereby produces an agreeable refreshing or cooling effect in the mouth.

In addition to its cooling effect, xylitol has interesting sweetening qualities. If one takes sucrose as a reference point, and attributes to it a sweetening value of 1, xylitol is found to have a sweetness of the same order. Thus, xylitol is a sugar substitute. In fact, it has the same sweetness and bulk as sucrose with one third fewer calories (2.4 calories per gram) and no unpleasant after taste. It is currently approved around the world for use in foods, pharmaceuticals and oral hygiene products. For example, xylitol has been widely used in confectionery, baking products, cereals, desserts, jams, beverages, chocolate, chewing gum, gumdrops, and ice cream to name just a few products. It has also been used in the production of oral hygiene products, such as toothpaste and in pharmaceutical products. In addition, it is used as a sucrose substitute placed in foods for consumption by people with diabetes.

Further, xylitol has an interesting property for dental health, in which it differs from other known polyols. It is, in fact, anti-cariogenic, i.e., it cannot serve as a substrate for bacteria present in the mouth cavity. Moreover, it also plays a role in preventing dental caries. It inhibits the growth of *Streptococcus Mutans*, the primary bacteria associated with dental caries. Recent interest has increased in xylitol-containing candies because xylitol has been shown to promote remineralization of teeth and damaged tooth enamel. It has also been found that regular use of xylitol can inhibit the transfer of cariogenic *Streptococcus Mutans* bacteria from mothers to their newborn children. Studies have shown that mothers are the primary source of infection of *Streptococcus* in the mouths of newborns and that prevention or delaying colonization by these bacteria leads to significant reduction in tooth decay later in life. In addition, xylitol reduces plaque accumulation and inhibits plaque regrowth.

Further, it also increases salivary flow. Saliva helps clean and protect teeth from decay and this plays a role in repairing the damage caused in the early state of the decay process.

Thus, it is important to have a method of producing products comprising xylitol for use in these various applications.

One such product is a hard candy comprised of xylitol. However, producing a hard candy of xylitol is challenging. It is difficult for xylitol to be made into a hard candy free of crystals because its glass transition is below 32 F (0 C) and at normal household conditions, it would exist as a liquid, although because of its instability, would slowly transform to a few large crystals grown loosely together. Furthermore, as a crystal, it does not compact well.

In addition, in preparing hard candies comprising xylitol, the xylitol is traditionally melted completely to form a molten mass. The molten mass is mechanically agitated or seeded with xylitol crystals to cause crystallization. The resultant seeded mass is then combined in a layered format, wherein an isomalt base is first deposited, then followed by a xylitol layer or the xylitol is codeposited with isomalt in a mold to produce hard candy.

The problem often encountered in this process is that the final product is usually hygroscopic and sticky. Further, the molten mass often manages to crystallize in the machinery and/or equipment, thereby clogging the machinery and/or equipment. Further, once the seed crystals have been added, the viscosity of the seeded molten mass is very difficult to control. Moreover, the product is very temperature sensitive. The seeded mass thickens and crystallizes rapidly if the temperature falls below the melting point of xylitol, and on the other hand, thins, due to melting of the seed crystals if the temperature is raised above the melting point. As a consequence, the viscosity and density of the seeded mass tends to vary upon prolonged exposure to a molten state which is particularly undesirable in deposited hard candy manufacturing lines where any inconsistency of the seeded mass leads to inconsistent piece weight and potential equipment failure. Further, the resultant candy is quite hard, and difficult to bite through.

The present inventors were investigating a new method for producing a hard candy comprising xylitol by modifying the methodology of the prior art. They began preparing the hard candy in a scraped surface heat exchanger, maintaining the temperature at or above the melting point of xylitol. Even though they initially worked with a complete melt, when they lowered the temperature in the scraped surface heat exchanger below the melting point of xylitol, crystals of xylitol began to form in the scraped surface heat exchanger and begin to clog the machine. Once the xylitol recrystallized, it became extremely difficult to work with. The inventors also noted that the product was hard and was not easily bitten into. Moreover, the inventors have confirmed that if the temperature of the emitted scraped surface heat exchanger was too hot, such material was difficult to handle and the product obtained was undesirable.

However, the inventors found that if the xylitol was not completely melted in an extruder, the resulting product was different and was much softer than the product comprising xylitol obtained from completely melting the solid and recrystallizing the melted solid in a scraped surface heat exchanger. Further, in the method found by the present inventors, since the xylitol solid was not being recrystallized, the extruder was no longer getting clogged.

The present invention thus describes this process which overcomes the problems enumerated above and provides a product which has a high flavor impact and a strong cooling sensation. Yet, at the same time, the product that is produced is a soft product that can be easily bitten through.

SUMMARY OF THE INVENTION

The present invention, in one embodiment, is directed to a method of producing a solid non-compressible comestible product comprising xylitol, said method comprising:
(a) subjecting a composition comprising solid xylitol in an amount ranging from about 60% up to and including 100% by weight to extrusion treatment in an extrusion apparatus under conditions sufficient to partially melt the xylitol in the composition to form a slurry and maintain the composition as a slurry as it passes through and exits the extrusion apparatus, (b) forming the extruded product from step (a) into a desired shape and (c) cooling the product of (b) to form a solid.

The present invention is also directed to the product of the process described hereinabove. In an embodiment, it is a comestible comprising from about 60% to about 100% xylitol, having irregularly shaped crystals, and which, when molded into a yertz shape having a base width of 8.20 mm, a base length of 13.26 mm, a height of 8.71 mm, an angle of 10% between the vertical and the side and having 0.25 mm radius fillet and weighing about 0.75 grams, has a piece break pressure of less than about 110 MPa and a dissolution rate from about 200 to about 400 seconds, said comestible having a moisture content of less than about 1% by weight of the composition, said comestible being substantially free of monosaccharides and disaccharides and maltodextrin having a DE (dextrose equivalent) of less than 20 and sugar alcohols other than xylitol.

BRIEF DESCRIPTION OF THE DRAWINGS

FIGS. 2a, 2b and 2c each depict a cross section of the extruder system in FIG. 1.

FIG. 3 is an embodiment of a depositor.

FIG. 6a is a front view, while FIG. 6b is a top view and FIG. 6c is a side view.

DETAILED DESCRIPTION OF THE INVENTION

Figure 1:
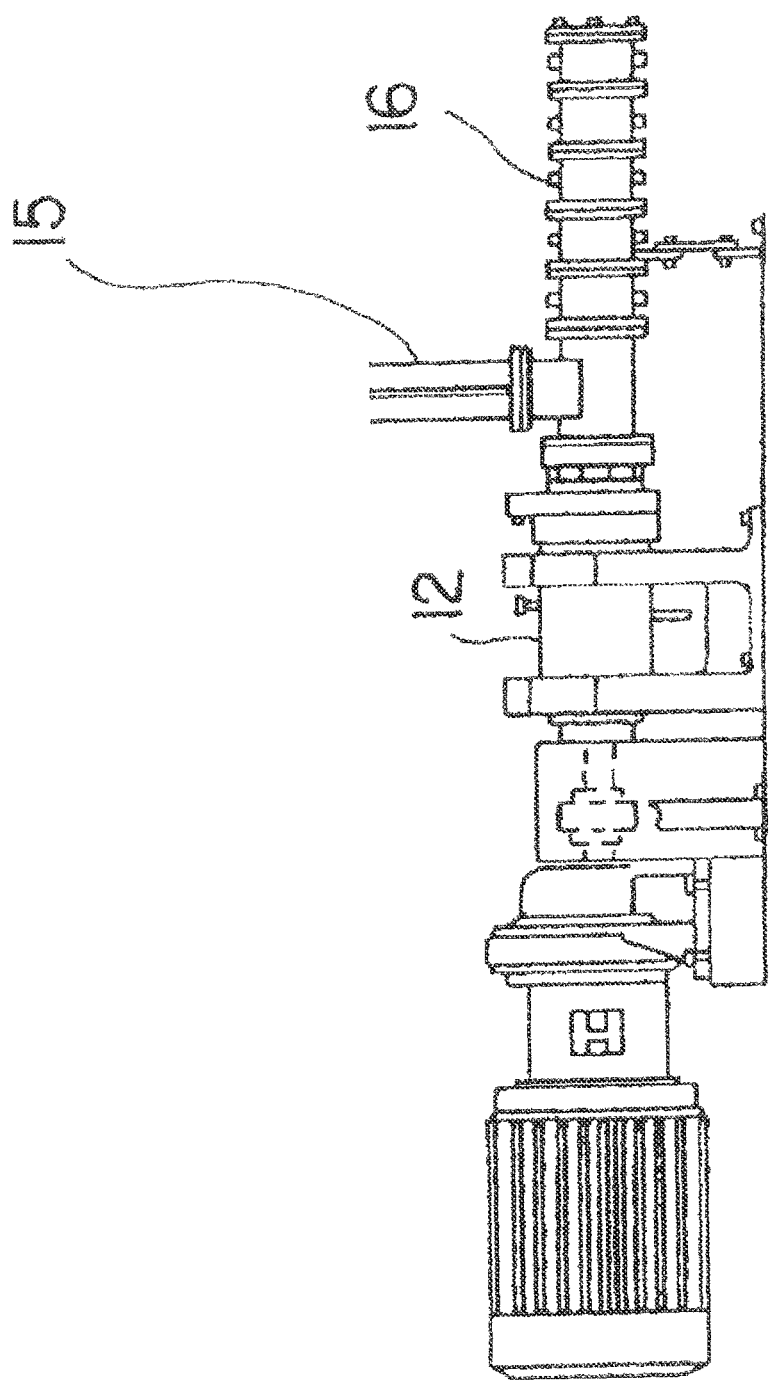
FIG. 1 illustrates a single screw extruder system that can be utilized in the present invention.

As described hereinabove, an embodiment of the present invention is directed to a process of preparing a comestible product comprised of xylitol. The comestible product within the scope of the present invention includes hard candies, drops, such as fruit drops or cough drops or candy drops, and the like or any molded shaped product comprised substantially of xylitol. Alternatively, the comestible product may be a pharmaceutical. The product may be uncoated or coated with coatings normally used in the confectionery arts. In an embodiment, the product, including the coating, is substantially sugar free, e.g., contains no sugar, such as sucrose. As used herein, the term "sugar" refers to aldoses and ketoses, which are monosaccharides or disaccharides.

These sugars which are excluded include, without limit, erythrose, threose, ribose, arabinose, xylose, lyxose, allose, altrose, glucose, mannose, gulose, idose, galactose, talose, erythrulose, ribulose, xyulose, psicose, fructose, sorbose, tagatose, maltose, lactose, sucrose and the like. By being "substantially free", it is meant that the product contains at most, if any, trace amounts of any sugar, i.e., the sugar content is less than about 1% by weight.

The major ingredient of the comestible product of the present invention is xylitol. Xylitol is commercially available in a crystalline form (or granulated form). Either form of xylitol may be used in the comestible product of the present invention.

The comestible product contains at least about 60% by weight xylitol. In one embodiment, the comestible product contains from about 60% xylitol up to and including 100% xylitol by weight and in another embodiment, from about 70% xylitol up to and including 100% xylitol by weight and in a still another embodiment from about 80% up to including 100% xylitol by weight. In another embodiment, the comestible product contains from about 85% xylitol to 100% xylitol by weight and in a still further embodiment, the comestible product contains from about 90% xylitol up to and including 100% xylitol by weight. In a still further embodiment, the comestible product contains from about 95% xylitol up to and including 100% xylitol by weight. Thus, in one embodiment, the comestible product contains solely xylitol.

In one embodiment, the xylitol is in association with another active product, e.g., a pharmaceutical. In an embodiment, the composition contains as much drug as possible, for example, up to and about 40% by weight drug. In an embodiment the composition comprises from about 0.01% to about 40% by weight drug, and at least about 60% xylitol by weight such as, for example, from about 60% to about 99.99% xylitol by weight When xylitol is the sole active ingredient or when the comestible product is a hard candy, drop or molded product, the objective is to maximize the concentration of xylitol. In an embodiment, the xylitol is present in at least from about 70% by weight to about 100% by weight and in another embodiment, the xylitol is present in amount varying from about 80% to about 100% by weight.

Besides xylitol, the comestible product optionally contains flavorants, such as one or more food grade acids that are conventionally used in confectionery products. In an embodiment, these flavorants are present in flavoring effective amounts. An example of a flavorant is food grade acid. In one embodiment, the one or more food grade acids are present in amounts ranging from about 0.01% to about 10% by weight of the product. In another embodiment, they are present in an amount ranging from about 0.01% to about 5% of the product, and in still another embodiment from about 2% to about 4% by weight of the product.

Examples of food grade acids that may be used in the present invention include, but are not limited to, malic acid, lactic acid, acetic acid, citric acid, fumaric acid, adipic acid, tartaric acid, ascorbic acid, phosphoric or salts of any of the food grade acids. The comestible composition thus may comprise xylitol and optionally one food grade acid or salt thereof or a combination of one or more food grade acids or salts thereof.

The comestible composition may optionally contain other ingredients normally found in confections. For example, the composition may additionally contain other compounds, such as vitamins, minerals or other dietary substances that have the proper stability, i.e. they are stable under the conditions for forming the comestible composition of the present invention. In addition, the composition may also contain other flavoring agents in addition to or in lieu of the food grade acids.

The other flavors useful in the present invention are flavors well known for use in comestible products, such as foods, e.g., confections. The flavorant may be in solid form, such as a powder, crystalline, amorphous crystal, semicrystalline and the like. They may be in the form of liquids or they may be encapsulated or they may be spray dried. The additional flavors include those derived from essential oils, as well as those flavors characterized as either natural or artificial flavors. Examples include essential oils such as, without limitation, cinnamon, spearmint, peppermint, birch, and the like; natural or artificial fruit flavors, such as, without limitation, apple, pear, peach, strawberry, cherry, apricot, orange, lemon, watermelon, banana, and the like; bean derived flavors such as, without limitation, coffee, cocoa powder and the like. In another embodiment, the flavoring agent may be a spice commonly used in foods. Examples include chili powder, curry powder and the like. In another embodiment, the flavorant may be a salt commonly used in the food arts, such as sodium chloride, potassium iodide, potassium chloride, sodium iodide and the like. In another embodiment, the comestible product of the present invention contains one or more flavorants.

However, those flavors derived from the essence of mint oils are preferred. In the instance where flavors, such as peppermint, spearmint and the like are prepared in accordance with the present invention, the resulting flavor composite yields a particularly cooling taste sensation. The cooling effect is attributable to the presence of xylitol in the solid crystalline form in combination with the mint oil. Thus, flavor enhancement is a further feature and benefit of the present invention.

As with the food grade acids, these flavoring agents are present in flavoring effective amounts. For example, they are present in amounts ranging from about 0.01% to about 10% by weight and in another amount from about 0.01% to about 5% by weight of the composition.

In addition, another optional ingredient is a cooling agent, i.e., an ingredient that imparts a cooling perception to the consumer when ingested. Examples include such agents as menthol, lemon aromas, WS 23, which is N,2,3-trimethyl-2-(1-methyl-ethyl)-butanamide, and the like. Even without the additional coolant, the comestible xylitol product dissolves quickly in the mouth and the coolness effect of the xylitol is felt by the consumer quite quickly. The additional coolant, if present, enhances the coolness effect felt by the consumer. In an embodiment, the cooling agent is present in an amount from about 0.01% to about 2% by weight of the composition and in another embodiment from about 0.05% to about 1% by weight if the comestible product.

However, some sugar alcohols are cooling agents. Nevertheless, the comestible product is substantially free of sugar alcohols other than xylitol. By substantially free, it is meant that if the comestible product contains a sugar alcohol other than xylitol, then the sugar alcohol is present in such low concentrations that it does not affect any of the properties described herein, such as the dissolution rate, the break pressure point, and the like. In one embodiment, the comestible product contains no sugar alcohol and in another embodiment, it contains trace amounts of sugar alcohol, for example, less than about 2.0% by weight of sugar alcohol, and in another embodiment, the sugar alcohol is present in less than about 1.0% by weight of the product. The cooling agents are those commercially available cooling agents normally used in the confectionery arts, except for the sugar alcohols other than xylitol, provided these other sugar alcohols are present in trace amounts, as described herein.

In another embodiment, the composition of the present invention is substantially free of sugars, such as monosaccharide, disaccharide and polysaccharide.

Cooling agents, when present, are present in an amount effective to enhance the coolness effect felt by consumers. In an embodiment, they are present in an amount ranging from about 0.01% to about 1% by weight of the product, and in another embodiment, are present in an amounts ranging from 0.01% to about 0.5% by weight of the comestible product.

There can also be added synthetic or natural food grade coloring agents, such as, for example but not limited to, azo coloring agents or carotenoids (e.g., B carotene, canthaxathin and the like), and the like.

The total amount of these coloring agents should not exceed about 5% wt of the composition. They may be present in as low as 0.001% by weight of the product.

In addition, sodium bicarbonate can also be present. Its presence effects dissolution and provides a unique texture to the composition. In an embodiment, when present, sodium bicarbonate reduces the density of the mixture. In an embodiment, the sodium bicarbonate is present in an amount effective to reduce the density of the composition relative to the density before addition thereof. In an embodiment, sodium bicarbonate is present in an amount ranging from about 0.01% to about 10%, and in another embodiment from about 0.01% to about 5% by weight, and in another embodiment from about 0.01% to about 3% by weight of the comestible product, Other additional components that can be present in the comestible product of the present invention include one or more food grade processing agents and food additives which are typically used in confectionery products. Examples include, but are not limited to, food grade preservatives, and the like. If present, they are present in amounts ranging from about 0.01% to about 5% by weight of the product.

These optional additives described hereinabove, such as food additives, e.g., food-grade acids, flavoring agents, coloring agents, food grade preservatives, and any other components that are typically used in confectionery products may be added as solids, or liquid form or may be pre-dried. The total amount of these optional ingredients, however, does not exceed about 40% by weight of the comestible product. In another embodiment, the total amount is no more than about 30% by weight and in another embodiment, no more than about 20% by weight, and in a still further embodiment no more than about 10% by weight of the comestible product and in another embodiment, no more than about 5% by weight of the comestible product.

Besides candy, the comestible product may be a pharmaceutical and may contain excipients known in the pharmaceutical arts. The pharmaceutical may be present in solid form, e.g., crystalline, semicrystalline or amorphous solid. The pharmaceutical may be a liquid. In addition, the xylitol in the comestible product may be present in combination with a pharmaceutical such as pain-killers, e.g., aspirin, as described herein. The pharmaceutical is present in a pharmaceutically effective amount. The amount can be as low as 0.01% or 0.05% by weight and up to and including about 40% by weight. The pharmaceutical is present in a pharmaceutically effective amount. For example, if the pharmaceutical is an analgesic, e.g., aspirin, the analgesic is present in an analgesic effective amount. In an embodiment, the pharmaceutical is present in an amount ranging from about 0.1 to about 40% by weight. In another embodiment, it is present in an amount of about 5 to about 35% by weight. In another embodiment, the pharmaceutical is present in an amount ranging from about 8% to about 32% by weight. As described hereinbelow, any pharmaceutical can be utilized as long as the pharmaceutical does not decompose under conditions, e.g., temperature conditions, described herein in making the comestible product of the present invention. When a pharmaceutical is present the xylitol may be present from about 60% to about 99.9% by weight. In another embodiment, the xylitol may be present in at least 90% by weight and in another embodiment in at least 80% by weight.

The comestible product of the present invention formed by the present process has a very low moisture content. In an embodiment, water is present in less than about 1% by weight of the comestible product. In another embodiment, it is present in less than about 0.5% by weight and in another embodiment, it is present in less than about 0.25% by weight.

An embodiment of the present invention is a comestible product comprising from about 90% to about 99.9% by weight of xylitol; and optionally from about 0.1% to about 5% by weight of one or more food grade acids. In another embodiment, the comestible product comprises from about 95% to about 99.9% by weight of xylitol; and in another embodiment, the comestible product comprises xylitol in about 95% to about 98% by weight and optionally from about 2% to about 4% by weight of one or more food grade acids.

In still another embodiment, besides the xylitol and optionally the food grade acid the comestible product additionally comprises a flavoring agent. In an embodiment, it additionally comprises from about 0.01% to about 10% flavoring agent by weight. In an embodiment, the comestible product comprises at least about 60% to about 100% by weight xylitol, optionally a flavoring agent, optionally cooling agent or both optionally flavoring agent and cooling agent. For example, in an embodiment the comestible product comprises at least about 95% xylitol, about 0.1 to about 2% flavoring agent and about 0.1 to about 0.5% cooling agent by weight.

In a further embodiment, the comestible product comprises xylitol and optionally one or more food grade acids, as described hereinabove and optionally a food coloring agent and a cooling agent. In a still another embodiment, the xylitol comestible product comprises xylitol and optionally one or more food grade acids in the amounts as described herein and about 0.001% to about 5% coloring agent.

In still another embodiment, the comestible product comprises xylitol, optionally one or more food grade acids and a coloring agent and a flavoring agent other than food grade acid and a cooling agent, as described hereinabove.

In yet another embodiment, the comestible product of the present invention comprises from about 90% to about 99.9% by weight of xylitol, optionally from about 0.01% to about 5% by weight of one or more food grade acids, and from about 0.01% to about 3% by weight of sodium bicarbonate. A coloring agent may additionally be present.

In an additional embodiment, the comestible product of the present invention comprises from about 90%, to about 99.9% by weight of xylitol, optionally from about 0.01% to about 5% by weight of one or more food grade acids, from about 0.01% to about 10% by weight of one or more food grade flavoring agents, and from about 0.01% and about 3% by weight of sodium bicarbonate wherein the total of the additives, e.g., flavoring agents, coloring agents and sodium bicarbonate, does not exceed about 20% by weight of the comestible composition.

In a still further embodiment, the comestible product of the present invention comprises from about 60% to and including 100% by weight of xylitol, and optionally contains from about 0.01% to about 5% by weight of one or more food grade acids, and optionally up to about 39.99% by weight of one or more food grade processing agents and food additives.

It is to be understood, as used herein, that 100% xylitol refers to the xylitol from a very substantially pure sample (e.g., having a xylitol concentration of greater than about 99.5% by weight) being the sole component. It may contain trace amounts of other components when manufactured, i.e., less than 0.5% by weight, but the preparation of the comestible composition, in accordance with the procedure hereinbelow does not add any additional components.

The comestible product is prepared by utilizing techniques known in the art, although the actual procedure was not known heretofore. In the first step, the composition comprising xylitol is placed into or fed into or passes through an extruder. If the composition contains optional ingredients, i.e., ingredients other than xylitol, a mixture comprising the xylitol and the other ingredient is prepared by blending the xylitol solid and the optional ingredients, e.g., cooling agent, flavoring agent, and the like to form a substantially homogeneous mixture, i.e., all of the ingredients are mixed thoroughly and are at least substantially uniformly dispersed in the mixture. In another embodiment, the various ingredients are uniformly mixed. The components are mixed in an apparatus typically used in the art, for example, a mixer, blender, shaker or static mixer and the like.

This mixing may be effected in a mixer separate from the extruder, i.e., it may take place prior to the mixed composition being placed into the extruder. In another embodiment, the mixing takes place within the extruder. The extruder has regions, such as a mixing zone, and the xylitol with any additional components introduced into the mixing zone from a feed device, e.g., feed hopper, pump and the like, is subjected to shearing force and intense mechanical friction by the compression in the turns of the screw. The blended xylitol composition enters the extrusion stream and is subjected to the processes described hereinbelow.

This composition or if xylitol is the sole component, xylitol (hereinafter, the composition being drawn through in the extruder will be referred to as the "extruder composition") is subjected to additional processing as described below. The extruder optionally contains at least one extrusion die, although it is not necessary. Inside the extruder, there are at least one or more temperature zones which are set to predetermined temperatures. In the present process, the temperature zones are set at temperature to partially melt the xylitol so that in the extruder, the extruder composition is only partially melted, that is, the xylitol is molten and contains crystalline solid. By "partially melted", it is meant that the mixture is not completely melted. In other words, some solid material, xylitol, is maintained and not completely melted. In accordance with the present process, seed crystals are not necessary. In an embodiment of the present process, at least about 10% by weight of the solid is melted, while in another embodiment at least about 50% by weight of the solid is melted. In a still further embodiment, at least about 90% of the solid is melted. In a further embodiment, at least about 95% of the solid xylitol is melted. As indicated hereinabove, in each of the embodiments in the present process, in the extruder, not all of the solid xylitol is melted, that is, less than 100% of the solid xylitol is melted.

It is essential that not all of the xylitol in the composition is melted. As explained hereinbelow, the product contains crystals of various sizes. Some are large and others are small. If all of the xylitol in the extruder composition is melted, then upon cooling, recrystallization will occur, creating the problems described hereinabove, which problems are to be avoided. If the xylitol crystallizes in the extruder, it causes the apparatus to be clogged.

The partial melting of the extruder composition in the extruder is effected at a temperature and for sufficient amount of time so that only a portion of the solid is melted, as described herein. In an embodiment, the temperature of the extruder composition in the extruder ranges from about 190 F to about 205 F and in another embodiment from about 194 to about 200 F. The temperature at which the extruder is to be set so that the slurry is in this temperature range is easily determined by one of ordinary skill in the art.

By "slurry", it is meant a translucent mass in a slushy like state. As a slurry, it contains a heterogeneous mixture of the ingredients described hereinabove in solid and liquid form. For example, it comprises xylitol solid mixed in with xylitol liquid and any optional ingredients. As indicated below, the mixture remains a slurry and is not completely melted in the extruder.

The partial melting is effected in the extruder. It can be a single screw extruder, a twin screw extruder or multi-screw extruder, commonly used in the confectionery arts. The extruder may have various temperature zones. Generally, the various temperature zones are sufficiently high as described above, to effect the formation of the slurry and to achieve a partial melting of the xylitol therein. The extruder composition in the extruder is at a temperature sufficiently high so that the composition is partially melted but sufficiently low so that it does not all melt. In addition, in the exit zone (also known as the discharge zone), the temperature thereof is sufficiently high so that the partial melt is maintained and sufficiently low so that the xylitol does not all melt. In an embodiment, the slurry in the exit zone of the extruder is at a temperature ranging from about 190 F to about 205 F, and in a still further embodiment, from about 194 F to about 200 F.

In the partial melting step, the mixture is in a partial molten state, forming a slurry and remains in the slushy state. The mixture is maintained at the appropriate temperature range at or about the melting point of xylitol for a sufficient amount of time to form a slurry and maintain the consistency of the slurry in a slushy state in and through the extruder and subsequent processing. If the temperature of the slurry is too low, then the slushy mixture would result in rapid crystallization and uncontrolled hardening of the slushy mixture and possible clogging of the equipment. If the temperature of the slurry is too high, then more of the slush may melt and the slushy state may not be maintained.

The slurry may be further processed to form the desired product by methods commonly used in the confectionery industry, for example, depositing or molding. However, prior to being molded or deposited, the slurry, in one embodiment, is transferred to the depositor. A predetermined amount of the slurry, such as in the form of a drop or sheet, is deposited onto a belt. In another embodiment, the slurry is placed into a mold. However, prior to reaching the mold or prior to the extruded composition being deposited onto a belt, the slurry is maintained at a temperature so that it remains a slurry. In an embodiment the slurry is maintained at or about the same temperatures as when present in the exit zone or as it exits from the extruder. In an embodiment, the slurry is maintained initially, after it exits the extruder at about 190 F to about 205 F and in another embodiment, about 194 F to about 200 F by conventional methods known to one of ordinary skill in the art, such as by jacketing the equipment with heating means.

In carrying out the process, the mixture in an embodiment is maintained in a relatively dry atmosphere to prevent moisture pick up such that the moisture content does not exceed about 1% moisture.

This process of the present invention is described hereinbelow in greater detail by referring to the drawings. The extruder contains a feeding device, for example a feed hopper or feed screw, at least one outlet in the discharge zone from which the extruder composition leaves the extruder and in between, an extrusion barrel connecting the feed hopper to the outlet and which contains mixing and kneading regions and means of thermal regulation of the mixing and kneading regions to control the temperature of the mixing regions.

Figure 2A:
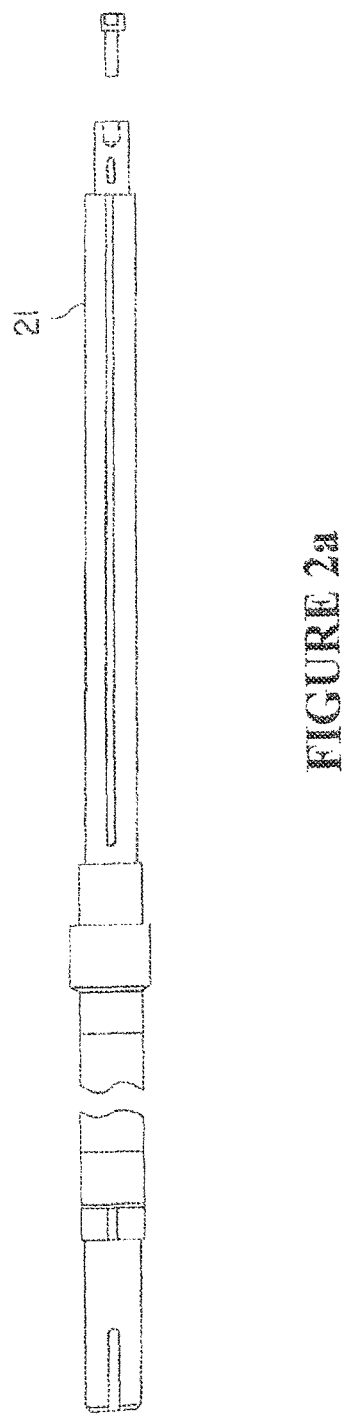

An example of an extruder (12) for use in this invention is depicted in FIG. 1. It is a single screw extruder and it has a vertical feed screw (15) which forces the extrusion composition into the extrusion section (16) of the extruder (12). FIGS. 2a, 2b and 2c illustrate cross-sectional views of the of the extruding section of a single screw extruder (12). As depicted in FIG. 2a, the extrusion section of a single-screw unit is driven by a central longitudinal shaft 21 onto which screw segments 22 and steamlocks 23 are affixed to the shaft (See FIG. 2b). The screws 22 and heating means, e.g., electric resistors or heating systems operated by induction or steam, are affixed. In FIGS. 2a, 2b and 2c, the heating means is a heating system operated by steam. The steamlocks 23 are arranged to provide a progressively tighter pitch and greater resistance from the inlet zone to the outlet zone. This arrangement results in the development of a continually increasing pressure gradient. The barrel segments 24 (FIG. 2c) are consecutively affixed onto the extruder housing and are jacketed to receive either steam or cooling water. These jacketed barrels assist in the development and control of the temperature in the extruder. Each screw segment 25 is positioned within a corresponding barrel segment 24 to make up a designated zone. The shaft 21 revolves at variable speeds within the barrel to establish the required shearing conditions.

The extruder as shown can have a number of temperature zones. The embodiment depicted in FIG. 1 has six zones in a single-screw extruder. Each zone is provided with a separate double jacket. The first zone in the extruder 12 is the inlet zone and the last zone is the discharge or exit zone. The inlet zone contains a wide flight tapered screw designed to direct the feed mass into the barrel housing. Zones two, three, and four desirably have screws with intermediate flight spacings intended to convey and compress the mass. Zones five and six are equipped with "tight flight" screws. The tight flight screws work and compress the mass. The discharge zone includes an exit die head. The exit die head contains multiple hole outlets to release the extruded mass to the atmosphere.

The extrusion composition is charged into the inlet zone of the extruder 12. Due to the extremely high total surface area and low moisture content of the extruder composition, particle-to-particle friction caused by the mechanical shear of the rotating screw shaft 21 generates sufficient heat to rapidly increase the temperature of the mass in the extruder barrel. If the mass is heated up too quickly, various feed-flow problems, including the possibility of material blow-back, can occur.

In FIG. 2 zones two and three are water-cooled jackets that decrease the rate of temperature rise of the extruder composition and prevent the problems described hereinabove in the background of the invention. Even with these water-cooled jackets, the temperature of the extrusion composition in the extruder is sufficient to maintain the xylitol as a slurry, i.e., a mixture of molten xylitol and crystalline xylitol. In an embodiment, the temperature of the slurry is maintained about the melting point of xylitol. e.g., about 190 to about 205 F, while in an embodiment from about 194 to about 200 F. However, the temperature of the extruder is increased from friction within the extruder barrel. The extrusion composition is kneaded in zones two and three and conveyed to zone four. In the extruder e.g., in zone four, the extruder composition is compressed and further heated, but the extrusion composition is and remains a partial melt, a slurry. Zones four, five, and six have steam-heated jackets that may, correspondingly, increase the amount of liquid phase, but the extruder composition still remains a partial melt. The temperatures of zones four and five are usually controlled.

In another embodiment, the extruder is a twin-screw type extruder. In this embodiment, it has a feed hopper, as in the single screw extruder. It is a mixing device which kneads the mass, but instead of having one screw, it contains a twin screw system. It may optionally have an outlet die. But it also contains a means of thermal regulation similar to that depicted in FIG. 1. The starting material introduced into the mixing area is subjected to shearing forces and intense mechanical friction by the compression in the turns of the screw and at the same time to heating which is introduced by the heating means.

The twin screw extruder has heating zones, and the temperatures of the slurry in the various zones, including the discharge zone, are as described for the single screw extruder, discussed hereinabove. Again, as in the single screw extruder, the temperature of the slurry in the various temperature zones and in the discharge is at a temperature in which the xylitol forms a slurry and is maintained as a slurry. This, in one embodiment the temperature ranges from about 190 F to about 205 F, and in a further embodiment, from about 194 F to about 200 F.

Nevertheless, regardless of the type of extruder, the xylitol in the composition in the extruder and throughout the extruder and discharged from the extruder is only partially melted. As stated above, the extruder composition is not completely melted.

Next, the slurry discharged from the extruder is formed into the desired shape and then cooled. As described below it can any shape that is desired. For example, it may be pastilled, deposited on a belt, molded, or sheeted to form solid product of suitable size and shape. For example, the slurry may be extruded from the extruder, into a depositor, as described above. The bottom of the depositor has a mechanism to control the flow of materials therefrom, thus allowing it to be metered at a desired rate. For example, the area of the depositor contains pistons through which the slurry is fed and deposited onto a belt at a desired rate.

Reference is made to FIG. 3. FIG. 3 depicts the extruder discharging the slurry onto a hopper, which is part of the depositor. The depositor contains a plurality of pistons set parallel. The pistons are arranged so that the nozzles thereof pass through a manifold. The slurry is conveyed to the pistons.

While in the depositor, including the hopper, the partially melted slush is maintained as a partial melt. For example, it is maintained at a temperature ranging from about 190 to about 205 F and in another embodiment from about 194 to about 200 F. Although not shown, the depositor, (including the hopper and the area around the pistons) is jacketed with heating means, as described above with the extruder.

The pistons work with the nozzles to assure a set amount in the form of a drop is deposited onto the belt or into a mold Depositing the xylitol slush directly onto a belt produces a desirable rounded candy piece. In an embodiment, it produces a rounded candy piece (sphere) when the belt on which it is deposited has a contact angle above about 110° and less than about 180°. By contact angle, it is meant the angle at the point where the outside surface of the slurry from the depositor intersects or meets the belt. In another embodiment, the contact angle ranges from about 120° to about 180° and in another embodiment from about 135° to about 180°.

The slurry discharged from the extruder may be deposited onto a belt or into a mold to form a solid product of suitable size and shape. In an embodiment, the slurry extruded from the extruder is deposited into molds having suitable shapes and sizes.

When placed into a mold, the slurry is cooled to a temperature where the slushy composition is a temperature at which it solidifies, e.g., it is below the temperature of 190 to about 205 F to allow the xylitol contained therein to harden.

Figure 6A:
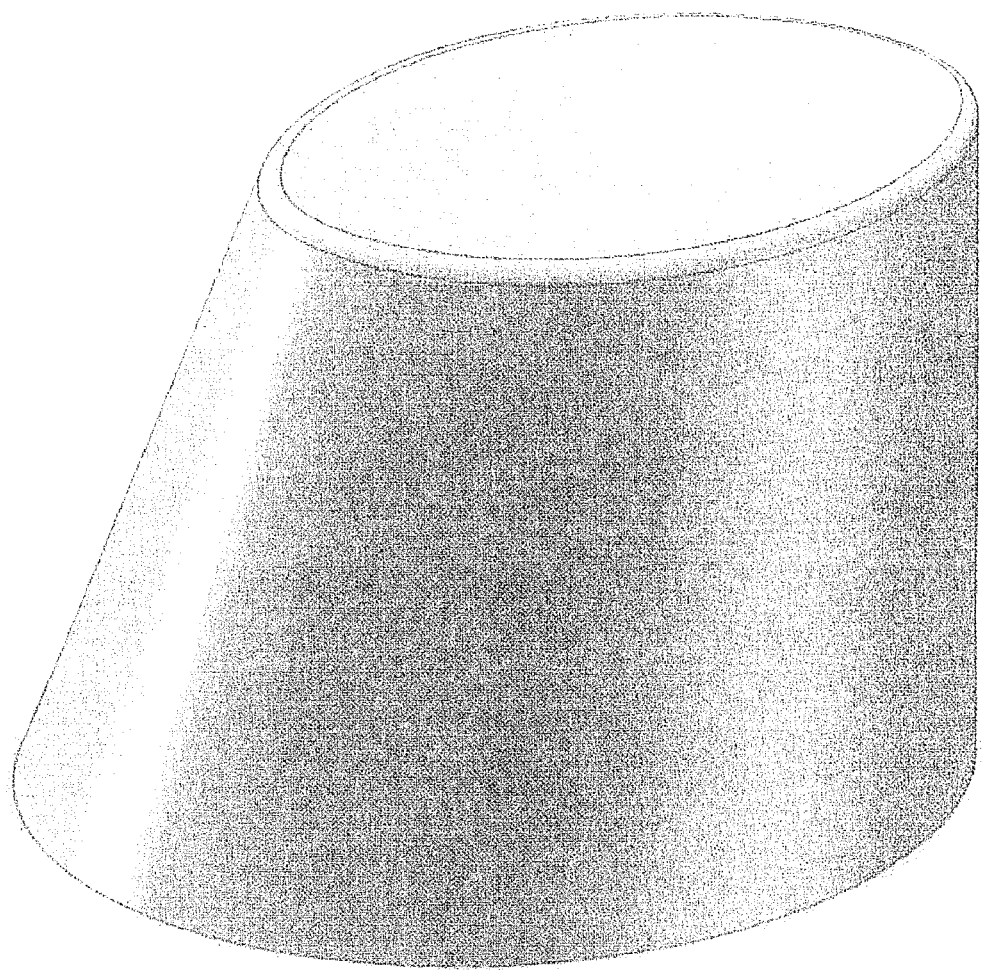
FIGS. 6a-6c represent photographs of a xylitol composition molded into a yertz shape.
Figure 6B:
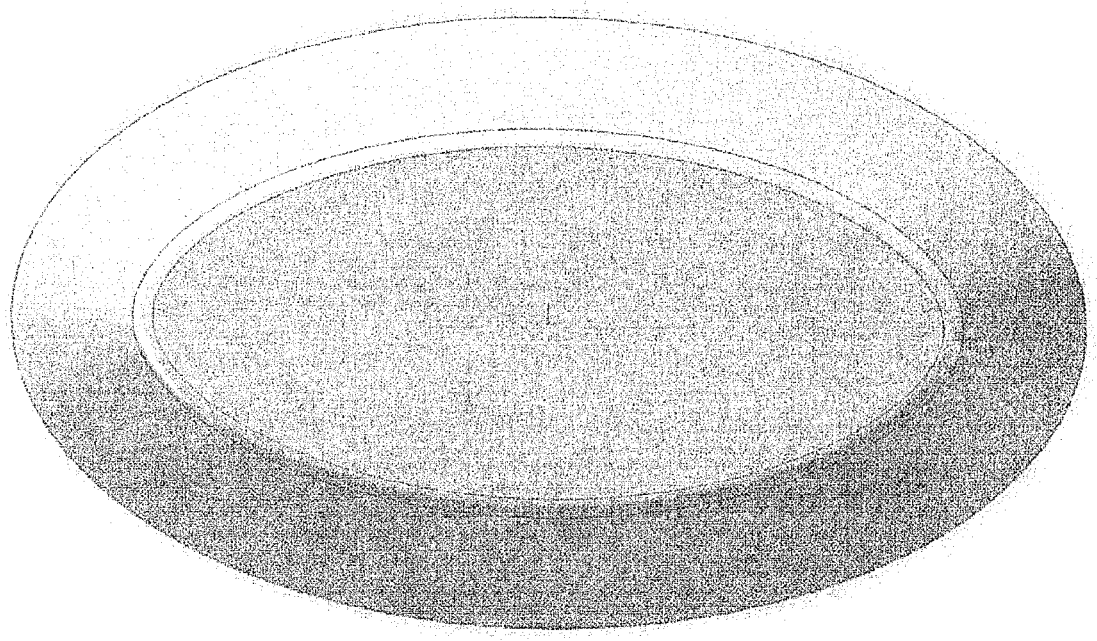
Figure 6C:
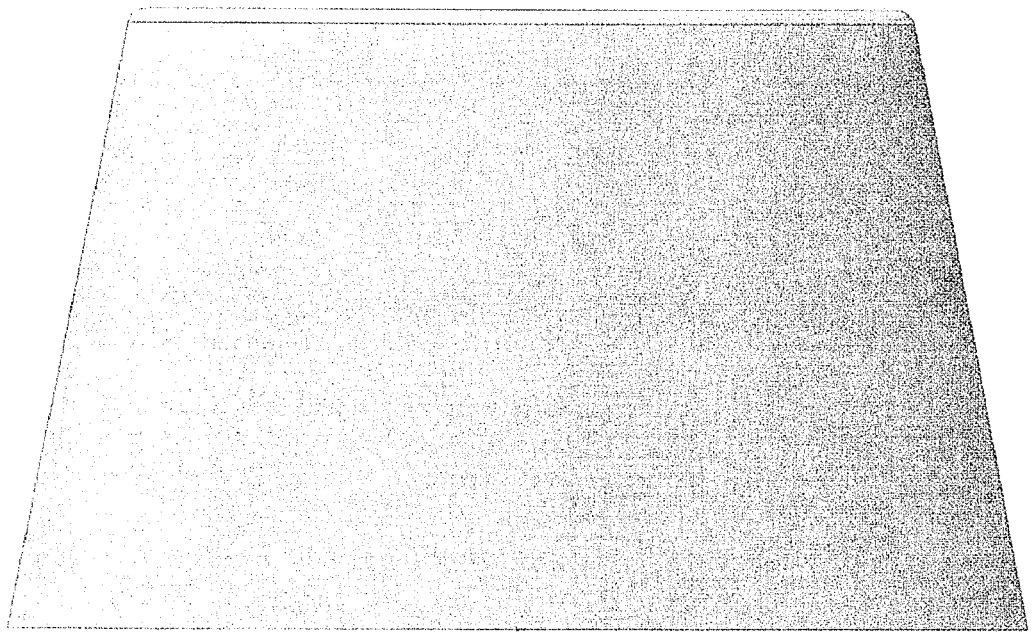

The final product from the mold or belt may be formed into a variety of shapes that include, but are not limited to, spheres (discs), hemispheres, cubes, cuboids, pyramids, squares, rectangles, triangles, octagons, hexagons, pentagons, prisms, or a yertz, which is an elliptical cylinder which is wider at the top than at the bottom or any other desired shape. A picture of the yertz shaped product is depicted in FIGS. 6a-6c. Alternatively, the final product from the mold or belt may be formed into an irregular shape.

Once the mixture is formed into the desired shape, the formed product is cooled. This can be effected, for example, by allowing the temperature of the slushy material to fall below the melting point of xylitol, for example, below about 190 F. Temperatures as low as ambient temperatures may be used to cool the slurry to crystallize it. For example, the slurry may be passed through one or more cooling tunnels to gradually cool the formed product to room temperature. In an embodiment of the present invention, air is employed as a cooling medium. Air used for cooling should not be too cold to avoid sweating. In an embodiment of the invention, the temperature of air is between about 68 F and about 104 F.

In another embodiment, air at a temperature of less than about 190 F is utilized to cool the final product. That is, the product is allowed to stand until it completely solidifies. The cooled solidified product may optionally be grinded to whatever size desired.

In the present process, once the temperature of the slurry is below about 190 F, it takes less than about ten minutes for the xylitol in the composition to completely solidify. In another embodiment, it takes less than five minutes for the xylitol in the composition to completely solidify once the temperature is lowered to less than 190 F, while in another embodiment it take about two to about three minutes to solidify.

The formed comestible product is then packaged. Conventional packaging materials and methods can be used for packaging the comestible product of the present invention based on the size and shape of the comestible product.

It is to be noted that the percentage by weight of the composition of the present invention remains about the same throughout the process. Thus, for example, if the mixture in the first step contains about 60% xylitol, the mixture in the slurry contains xylitol at about 60% by weight and the final product contains about 60% by weight.

The moisture content throughout the process remains at about constant. More specifically, in an embodiment, the moisture content is less than about 1% by weight, and in another embodiment, is less than about 0.50% by weight and in a still further embodiment is less than about 0.25% by weight.

The product formed from the present process comprises at least 60% xylitol by weight. It has a low moisture content, less than about 1% by weight. Further, the dissolution rate of the product formed by the present process is dependent upon many factors, including the shape and weight of the product and the temperature of the solvent, usually water, in which the dissolution rate is determined. By dissolution rate, it is meant as the time required for predetermined amount, such as 0.75 gram, to completely dissolve. Although the product may be any shape or size, for purposes of describing a characteristic of the product, a 0.75 gram piece, when molded into the shape of the yertz, as shown in FIGS. 6a-6c, having the following dimensions: a base width of 8.20 mm, a base length of 13.26 mm, a height of 8.71 mm, an angle of 10° between the vertical axis and the side (that is, the angle between the base and the side is 80°) and 0.25 mm radius fillet, has a break pressure point of less than about 110 MPa. In one embodiment, the average break pressure of such a piece ranges from about 30 to about 105 MPa, and in another embodiment, from about 40 to about 100 MPa. The dissolution rate of this sample in a 37 C bath of water ranges from about 200 seconds to about 400 seconds, and in another embodiment from about 250 seconds to about 350 seconds and in another embodiment, from about 290 seconds to about 320 seconds.

The product formed from the present process is quite unique. It has irregularly shaped crystals. It is comprised of crystals of various sizes, wherein the size of the larger crystals is substantially larger than the size of the smaller crystals. In an embodiment the larger crystals range from about 400 to about 600 micrometers. These various sized crystals are randomly dispersed throughout the product. Because of the various crystal sizes and the looseness of the crystals in the product, the product of the present invention is not very hard. The presence of the large size crystals makes the comestible product of the present invention breakable without significant effort. When placed in the mouth of the consumer, the comestible product of the present invention melts rapidly and the consumer feels the cooling effect and flavor more readily than if the same product was prepared by conventional methods in which the xylitol is completely melted and then recrystallized. Further such a product prepared by the latter method is substantially harder than the product prepared by the present process.

In an embodiment, the comestible product of the present invention is substantially free of any sugar alcohol other than xylitol. Examples of the alcohols that the comestible product is substantially free includes glycol, glycerol, erythritol, threitol, arabitol, ribitol, mannitol, sorbitol, dulcitol, iditol, isomalt, maltitol, lactitol, polydextrose, polyglycerol, and the like. It contains at most trace amounts of flavorants containing those sugar alcohols. The comestible product is substantially free of and in an embodiment does not contain any aldoses and ketoses, including sugars, such as glucose and sucrose and contains ≤2% Maltodextrin having a DE of less than 20. In another embodiment, the present composition is substantially free of maltodextrin, (≤1%).

The product formed is non-compressible and is preferably not a tablet, although it can be in the shape of a tablet. Therefore, no binding agent or lubricant is present in the composition. It has a crunchy texture. By non-compressible it is meant that the product will break into pieces if compressed.

The product produced may be used as a pharmaceutically active compound. As employed herein the term "pharmaceutically active compound" refers to an organic or inorganic orally ingestible compound which is taken for medicinal, dietary and nutritional purposes and which is particulate in form. As described hereinabove, xylitol has several beneficial features in dental hygiene. Thus, in one embodiment, the comestible product is a pharmaceutical composition comprising a pharmaceutically effective amount of xylitol. As indicated hereinabove, in an embodiment the product contains at least about 80% by weight xylitol. The pharmaceutical composition also contains excipients normally found in the pharmaceutical arts.

Alternatively, the comestible composition comprises a pharmaceutically effective amount of a pharmaceutically active compound and excipients normally found in the pharmaceutical arts present together with the xylitol. Many drugs, such as aspirin, when placed in the mouth dissolve, leaving a horrible taste in the mouth. By adding a pharmaceutical to the present composition, it is much easier to ingest because the present composition masks the flavor of the pharmaceutical and makes the taste pleasant because of the cooling effect of the present composition. Any pharmaceutical may be utilized, as long as it does not decompose under the process conditions utilized. The drugs utilized are NSAIDS, over the counter drugs and prescribed drugs. Examples include, but are not limited, to pain relievers, such as salicylates: aspirin (also called acetylsalicylic acid or ASA), choline salicylate, magnesium salicylate, and sodium salicylate and the like, acetaminophen; nonsteroidal anti-inflammatory drugs (NSAIDs: ibuprofen, naproxen sodium, and ketoprofen), and the like; antihistamines, such as, loratadine, brompheniramine, chlorpheniramine, dimenhydrinate, doxylamine, and the like; decongestants, such as pseudophedrine, phenylephrine, and the like; laxatives, including bulk forming laxatives such as methylcellulose, polycarbophil, psyllium, and the like; stool softener laxatives, such as docusate sodium and the like; saline laxatives, containing non-absorbable ions, such as magnesium, sulfate, phosphate and sodium and the like, e.g., magnesium hydroxide, magnesium citrate, sodium phosphate and the like; stimulant laxatives, such as, bisacodyl, sodium bicarbonate and potassium bitartrate, sennosides, senna, and the like; antimetics, such as meclizine hydrochloride (Bonine), dimenhydrinate (Dramamine) and the like; oral nasal decongestants, such as drixoral nasal decongestants and the like; cough suppressants, such as dextromethorphan, guaifenesin, and the like; vitamins and minerals; antidiarrheal such as adsorbents, e.g., attapulgite, polycarbophil, and the like; anti-motility antidiarrheal, such as loperamide (Imodium) and the like; bismuth compounds, such as bismuth subsalicylate (Pepto-Bismol), and the like; drugs for treating acid ingestion, such as simethicone (Phazyme; Flatulex; Mylicon; Gas-X; Mylanta Gas), activated charcoal, and the like.

If an additional pharmaceutically active agent is to be present, it is prepared as described above for the comestible product. In one embodiment, the pharmaceutical is an analgesic, e.g., aspirin. The pharmaceutically active agent is blended with solid xylitol and with any other pharmaceutically acceptable excipients that are normally used and the mixture is then put into an extruder as described above. In this embodiment, the xylitol is the pharmaceutically acceptable carrier. As described hereinabove, the xylitol in the composition is partially melted in the extruder. The parameters discussed above for the extruder are applicable here, including the temperature of the extruded composition slurry in the discharge zone and as the slurry exits the extruder. In other words the temperature of the slurry in the exit zone ranges from about 190° F. to about 205° F. and in another embodiment from about 190° F. to about 200° F. Once the slurry is discharged from the extruder, it may be deposited, molded or pastilled. Subsequently, it is cooled and optionally milled to the desired size. The composition contains the medicament in effective amounts. The composition contains up to about 40% by weight of the pharmaceutically active compound and up to about 60% xylitol. For example, in an embodiment it contains as little as 0.01% medicament up to about 40% by weight medicament and in another embodiment from about 1% to about 38% by weight medicament. In such embodiments, the amount of xylitol ranges from about 60% up to about 99.99% xylitol and in another embodiment from about 62% up to about 99% by weight of the composition.

Unless indicated to the contrary, the term "extruder" and "extruder apparatus" are synonymous and are used interchangeably. In addition, the exit zone of the extruder and the discharge zone of the extruder are synonymous and are used interchangeably.

Further, unless indicated to the contrary, all percentages are by weight of the composition.

Further, the plural denotes the singular and vice versa.

In addition, the terms "slurry" and "slush" and "slushy state" are being used interchangeability. These terms are meant to be synonymous.

Furthermore, the term "extrusion composition" refers to the composition that is put into the extruder.

The terms "extruder" and "extrusion apparatus", as used herein, are synonymous, and are being used interchangeably.

The term "substantially free", as used herein refers to the composition not containing a particular component or a very small amount, but if present, it does not affect any of the properties described herein. For example, in an embodiment, if the composition is substantially free of a component, refers to the component being present in less than about 2% by weight and in another embodiment less than about 1.0% and in another embodiment, less than about 0.1% by weight.

Unless indicated to the contrary, it is to be understood that the temperatures are in F.

The following examples further illustrate the present invention. They are not meant to limit the present invention.

Example 1

Granular xylitol (98.8% w/w), powdered cooling compound WS23(N, 2,3-trimethyl-2-(1-methylethyl) butanamide (0.2% w/w) and granular peppermint flavor (1% w/w) were dry blended in a small batch mixer at ambient temperature of about 65 F-75 F. The dry blending continued until a homogenous mixture was obtained. The dry blend mixture was then fed into a water jacketed cooled hopper which feeds the product into a single screw extruder (Wayne, Totowa, N.J. having a 24:1 L/D ratio, 1 inch diameter screw in a 3:1 compression ratio). The extruder has five temperature controlled zones through which the mixture passed. The temperature in the various zones was set at about the melting point of xylitol, and the discharge of the extruder was a 40% melted mass at 198 F. The mass was solidified in a mold in the shape of mold within 2-3 minutes after being placed into a mold that was then exposed to ambient air temperature. The product produced was a soft hard candy in the shape of a mold that was easily broken by biting into it.

Example 2

Granular xylitol (98.8% w/w), powdered cooling compound WS 23 (0.2% w/w) and granular peppermint flavor (1.0% w/w) were dry blended at ambient temperature of about 65 F-75 F. The dry blended mixture was fed into the single screw extruder described in Example 1. The extruder is temperature controlled in five zones, each temperature of the composition in each zone being about the melting point of xylitol. The discharge temperature of the product exiting from the extruder was about 196 F. The product discharged from the extruder was about 40% melted. The product, which was a slush, was gravity drained into a heated depositor hopper that maintained the xylitol near the melting point range of the xylitol, which is about 197.6-204.8 F. The product was then deposited onto a conveyer belt where it took about 2-3 minutes to solidify when exposed to ambient air temperature. The product is softer than a typical hard candy.

Example 3

This example measures the dissolution rate of samples. The following equipment was used:
1. 1000 mL Pyrex glass beakers
2. Octagon shaped PTFE coated 2" magnetic stir bar with molded-on pivot ring
3. VWR Advanced Multiposition Stirrer—Four position stir plate with adjustable speed controlled for all positions simultaneously by integral knob—Catalog #12621-022
4. Thermometer—Mercury filled, partial immersion (76 mm immersion), 0 C to 200 C range—calibrated against NIST traceable digital thermometer
5. Three position digital timer
6. Deionized water
7. Balance, analytical—range: 0-200 gram, sensitivity ±0.0001 gram
8. Balance, top loading electronic—range 0-3000 g, sensitivity ±0.01 gram.
9. Hot plate
10. 4 Liter Pyrex glass Erlenmeyer flask Deionized water was heated in 4 Liter Erlenmeyer to 37 C. 600 grams of the heated water was divided into three separate 100 mL glass beakers. Stir bars were placed into the beakers. The beakers were positioned on three positions of the Four position stir plate. The speed was adjusted using digital control to 200 revolutions per minute. The water temperature at the start and end of the dissolution procedure was recorded.

When a pre-weighted sample piece was dropped into each beaker, the timer was started.

When the entire piece visibly dissolved the elapsed time was recorded as dissolution time.

The procedure was repeated each time using clean beakers and fresh 37° C. water.

The results for three samples prepared as above are depicted below:

| Samples | Avg Dissolution Rate (s) | % Std Dev for Dissol. Rate | No. Measurements | Avg Sample Wt | % Std Dev for Wt | Pc Shape |
|---|---|---|---|---|---|---|
| 1 | 293 | 6% | 4 | 0.7237 | 1.40% | yertz |
| 2 | 582 | 7.70% | 4 | 0.8296 | 7.20% | yertz |
| 3 | 650 | 12% | 4 | 0.7505 | 7% | yertz |

The first sample (Sample 1) is the product of Example 2 described herein above. The second sample (Sample 2) is a sugar hard candy having a 60/40 Sugar/CS ratio:

The third sample (Sample 3) is an isomalt/HSH sugar-free hard candy.

Example 4

The moisture content was measured using the Karl Fischer titration method using a Brinkman Karl Fischer Titrator with homogenizer and dissolving the samples in a methanol formamide solution (3:1).

The water activity was measured as follows. Using a Instrumentation: Decagon Aqualab water activity meter connected to a computer running Aqualink Report Generator (Decagon Devices, Inc., Pullman, Wash.), the water activity was measured as follows:

(a) Standardizing measurement: A slush of potassium chloride crystals in distilled water is prepared such that the solution is saturated with potassium chloride and potassium chloride crystals are visible on the bottom of the saturated solution. This was equilibrated to room temperature and then placed into a small cup that was inserted into the drawer and placed into the instrument. The reading is adjusted to be 0.859 at 15 C, 0.851 at 20 C, 0.843 at 25 C or 0.836 at 30 C (L. Greenspan. 1977. J. Res. NBS—A. Physics and Chemistry, 81A(1):89) according to the reported temperature.

(b) Sample measurement: The instrument was set to report readings continuously. The sample is placed into a cup placed into the instrument. The water activity is reported as the value which does not change by more than 0.002 units between subsequent readings.

Using samples prepared in accordance with the present process described herein, the water activity of the samples was measured as follows:

| Samples | Moisture | Water Activity at 20 C. |
|---------|----------|-------------------------|
| 4       | 0.24%    | 0.59                    |
| 5       | 0.26%    | 0.50                    |

Background for Examples 5-8 and Comparative Example 1

The procedure for measuring the texture is as follows:

Equipment:

The equipment that was used was TA.XT2i (Stable Micro Systems, Ltd., Scarsdale, N.J.) fitted with a 30-kg measuring head with a maximum force reading of 36800 g. Pieces were placed on a raised platform (HDP/90 heavy duty platform, Stable Micro Systems, Ltd., Scarsdale, N.J.) set upon the top of the base of the instrument.

Piece shapes: The "beltDep" piece is formed in the shape of a disc (sphere) by depositing slush directly onto a room temperature belt which progressed through a cooling tunnel resulting in a piece with average height of 4.17 mm (standard deviation of 0.13-mm) and average weight of 1.00-g (standard deviation of 0.036-g). The "Yertz" piece is formed by depositing slush directly into an oval-cylinder piece with slanting sides (narrower at the bottom of the mould than the top) with a mould bottom that was flat and 5-mm across the narrow oval axis. The mould was scraped to remove excess slush immediately after filling before hardening. The average height is 8.79 mm (standard deviation of 0.11 mm) and average weight of 0.746 g (standard deviation of 0.014 g). The "mouldDep" piece is formed by depositing slush directly into a mould with a concave bottom resulting in a piece that is flat on the mould-free side and convex on the top. The average height is 5.3 mm (standard deviation of 0.66-mm) and the average weight was 1.46 g (standard deviation 0.22 g).

Fixtures

A 2 mm blunt cylinder (2 mmBlunt) (part P/2, Stable Micro Systems, Ltd, Scarsdale, N.J.) with 3.1615 $mm^2$ area; beveled blade (knife/guillotine blade of HDP/BS Blade set, Stable Micro Systems, Ltd., Scarsdale, N.J.) (bevelBlade) with 0.5-mm width of the flat area of the blade for contact with the sample The blade contact area is 0.5 mm times the length of the blade contacting the sample.

The procedure was as follows:

0.1 mm/s to a distance or strain that results in the piece breaking, withdrawn at 10-mm/s, recording 200-pts/s. The beltDep was oriented with the belt-side down and compressed with the 2 mm blunt probe. The yertz was oriented with the mould-free side face-down on the platform and the probe was placed on the flat-bottom-mould face. When using the beveled blade, the blade was oriented across the narrowest axis of the oval which resulted in a contact area of 5 mm long by 0.5 mm wide or 2.5 mm area. The mouldDep was oriented with the flat-mould-free face against the platform and the 2 mm-blunt probe was oriented at the apex of the convex top.

Analysis:

maximum force at failure. The force in grams was converted to pressure in MPascals by first dividing by the area of contact and then converting to MPascals by multiplying by 0.009807.

Software Data Collection:

Texture Exponent (Stable Micro Systems, Ltd., Scarsdale, N.J.)

Statistical Analysis:

Excel (Microsoft, Redmond, Wash.). Within a dataset, "min" and "max" are the minimum and maximum pressure observed, respectively. "Average" is the average value, while "median" is the $50^{th}$ percentile number when ranked from least to greatest. "STD dev" is the standard deviation of the data set and "95 CI" is the half-width of the 95% confidence interval for the dataset based on the standard deviation and 2-tailed t-distribution with the degrees of freedom of that dataset. "95UL" is the estimated the upper limit for 95% of all values represented by this dataset which is the sum of the average and 95CI.

Example 5

Xylitol with flavor was partially melted in a single screw extruder and the slush was formed into yertz-shaped pieces that were average 8.8 mm height and 0.75 g weight. The pieces were demoulded and tested 45 min, 25 hr, 7 day and 101 days after pouring into the mould. The resulting break-pressures were observed.

| | Observed break pressure of yertz shape from slush formed on a single screw extruder | | | |
|---|---|---|---|---|
| break pressure | number observed | | | |
| MPa | 45 min | 25 hr | 7 day | 101 day |
| <10 | 0% | 0% | 0% | 0% |
| <20 | 0% | 0% | 0% | 0% |
| <30 | 5% | 0% | 0% | 0% |
| <40 | 40% | 12% | 1% | 3% |
| <50 | 40% | 33% | 6% | 10% |

-continued

Observed break pressure of yertz shape from slush formed on a single screw extruder

| break pressure MPa | number observed | | | |
|---|---|---|---|---|
| | 45 min | 25 hr | 7 day | 101 day |
| <60 | 13% | 45% | 30% | 17% |
| <70 | 2% | 11% | 27% | 22% |
| <80 | 0% | 0% | 17% | 33% |
| <90 | 0% | 0% | 15% | 13% |
| <100 | 0% | 0% | 3% | 3% |
| >100 | 0% | 0% | 0% | 0% |
| count | 110 | 110 | 110 | 72 |
| min, MPa | 21.1 | 30.2 | 38.6 | 35.5 |
| max | 61.1 | 67.3 | 91.8 | 93.5 |
| average | 41.3 | 50.3 | 65.7 | 67.8 |
| median | 41.0 | 51.2 | 64.2 | 69.6 |
| std dev | 7.6 | 8.4 | 12.1 | 12.5 |
| 95CI | 15.0 | 16.6 | 23.9 | 24.9 |
| 95UL | 56.30 | 66.88 | 89.59 | 92.73 |

The data of Table 1 indicates that the average break-pressure does not change after the first 7 days after forming. The data indicates that 95% of individual piece break-pressure will be less than 93-MPa after 101 days. This is about $1/10^{th}$ of the hardness of dentine.

Example 6

Xylitol with some flavor and color was partially melted in a single screw extruder and the slush was fed into the hopper of a depositor, from which slush was deposited into the yertz mold. Break pressure was determined on the demoulded yertz pieces 45 minutes, 1 day and 7 days after depositing.

Observed break pressure of xylitol-flavor slush formed in a single screw extruder, transferred to a depositor hopper and then deposited into a yertz mould

| peak pressure range, MPa | proportion observed | | |
|---|---|---|---|
| | 45 m | 1 d | 1 w |
| <20 | 0% | | |
| <30 | 10% | | |
| <40 | 33% | 0% | |
| <50 | 43% | 20% | 0% |
| <60 | 11% | 40% | 40% |
| <70 | 2% | 40% | 40% |
| <80 | 1% | 0% | 0% |
| <90 | 0% | | 20% |
| >90 | | | 0% |
| count | 82 | 10 | 10 |
| min, MPa | 26.9 | 42.7 | 50.6 |
| max | 73.7 | 69.2 | 88.3 |
| average | 41.7 | 57.1 | 64.0 |
| median | 40.3 | 57.9 | 60.6 |
| std dev | 8.2 | 9.4 | 12.2 |
| 95CI | 16.3 | 21.2 | 27.5 |
| 95UL | 90.0 | 90.4 | 115.9 |

After 1 week, the average break-pressure is no different than if the mould were filled with slush directly from the single screw extruder. Based on the number of observations, 95% of pieces are expected after 1 week to have a break-pressure less than 116 MPa. With a larger number of observations as obtained in Example 1, it would be reasonable to reduce this 95UL to that of Example 5 since the standard deviation and average are essentially the same at 1 or more weeks.

Example 7

Xylitol-flavor slush was formed using the single-screw extruder and poured into three different moulds. The demoulded pieces were tested for break-pressure at ages between 7 and 27 weeks using either the 2-mm blunt probe or the beveled blade.

Comparison of xylitol pieces made from single screw extruder made in different shapes and anylyzed by two different probes

| formula shape test age | xylitol beltDep 2 mmBlunt 10 wk | xylitol beltDep 2 mmBlunt 7 wk | xylitol yertz 2 mmBlunt 27 wk | xylitol yertz bevelBlade 27 wk | xylitol mouldDep 2 mmBlunt 23 wk |
|---|---|---|---|---|---|
| break pressure | | | | | |
| <10 MPa | 0% | 0% | | | |
| <20 MPa | 6% | 0% | | | |
| <30 MPa | 36% | 30% | 0% | | 0% |
| <40 MPa | 20% | 30% | 5% | 0% | 5% |
| <50 MPa | 18% | 16% | 15% | 5% | 30% |
| <60 MPa | 12% | 10% | 35% | 0% | 45% |
| <70 MPa | 4% | 6% | 35% | 35% | 20% |
| <80 MPa | 4% | 4% | 10% | 30% | 0% |
| <90 MPa | 0% | 2% | 0% | 25% | |
| <100 MPa | 0% | 2% | | 5% | |
| >100 MPa | 0% | 0% | | 0% | |
| count | 50 | 50 | 20 | 20 | 20 |
| min, MPa | 17.2 | 21.0 | 37.9 | 42.8 | 34.4 |
| max | 74.8 | 96.1 | 71.9 | 97.3 | 66.7 |
| average | 37.0 | 41.5 | 57.3 | 73.3 | 52.7 |
| median | 34.5 | 38.4 | 57.9 | 72.1 | 53.1 |
| stdev | 14.6 | 16.7 | 9.3 | 11.2 | 8.0 |
| 95CI | 29.3 | 33.6 | 19.4 | 23.5 | 16.7 |
| 95UL | 66.2 | 75.1 | 76.7 | 96.8 | 69.4 |

The data indicate that there is some discrepancy between the 2 mm blunt probe and the beveled blade, with the estimated 95UL being slightly less for the 2-mm blunt probe. The data indicate that piece shape does not affect the 95UL break-pressure which remains under 80 MPa for the 2-mm blunt probe regardless of shape.

Example 8

A xylitol/flavor slush was formed using a twin-screw extruder and extruded into two different shapes. Each type was tested for break-pressure using two different fixtures. The yertz shape was tested using the beveled blade and the molded deposit was tested using the 2-mm blunt probe.

| Observed break pressure on two different shaped pieces formed by slush made by a twin-screw extruder | | | |
|---|---|---|---|
| shape | yertz | | discMould |
| test | bevelBlade | | 2 mmBlunt |
| age | 1 wk | | 8 mo |
| break pressure MPA | frequency | break pressure MPA | |
| <40 | 0% | <40 | 5% |
| <60 | 5% | <60 | 25% |
| <80 | 50% | <80 | 65% |
| <100 | 18% | <100 | 5% |
| <120 | 23% | <115 | 0% |
| <145 | 5% | >115 | 0% |
| >145 | 0% | | |
| count | 22 | | 20 |
| min, MPa | 49.0 | | 49.3 |
| max | 144.3 | | 82.7 |
| average | 84.8 | | 63.2 |
| median | 78.6 | | 62.8 |
| std dev | 23.4 | | 12.9 |
| 95CI | 48.7 | | 27.0 |
| 95UL | 133.5 | | 90.2 |

The data indicate that the twin-screw extruder formed pieces that had a higher 95UL break-pressure than those formed using the single-screw extruder. The estimated 95UL break-pressure is 30 and 20 MPa higher for beveled blade and 2-mm blunt probe fixtures, respectively.

Comparative Example 1

Hard candy both sugar and sugar-free described in Example 3 was formed into two different mould shapes and then tested with either the beveled blade or the 2-mm blunt probe. The maximum pressure observed for the beveled blade and 2-mm blunt probe was 144 and 115 MPa, respectively, due to the limitations of the TA.XT2i 30-kg sensing head.

| Sugar or Sugar-free hard candy was formed into either the yertz or moulded disc (discMould) and tested by two different test fixtures | | | |
|---|---|---|---|
| formula | sugar | sugar-free | sugar |
| shape | yertz | yertz | discMould |
| test | bevelBlade | bevelBlade | 2 mmBlunt |
| age | 4 d | | 4 d |
| | break pressure | | break pressure |
| range, MPa | proportion | | range, MPa |
| <40 | 0% | 7% | <40 | 5% |
| <70 | 13% | 29% | <70 | 0% |
| <100 | 13% | 7% | <100 | 5% |
| <130 | 13% | 14% | <115 | 5% |
| >130 | 60% | 43% | >115 | 85% |
| >144 | 47% | 29% | | |
| count | 15 | 14 | | 20 |
| min, MPa | 43 | 35 | | 33 |
| max | >144 | >144 | | >115 |
| average | 118 | 100 | | 109 |
| median | 138 | 106 | | 115 |

The data indicate a very wide range of break-pressures for hard candy that encompasses values beyond the capacity of the machine. The maximum break-pressure was greater than 144 and 115 MPa when measuring with the beveled blade and 2-mm blunt probe, respectively. This substantiates that the xylitol/flavor pieces made with the single-screw extruder have an upper limit break-pressure that is less than hard candy.

Example 9

Forming piece by depositing on a flat belt. On different samples of flat belt was placed on 10-20 micro-liter drop of 99.5% glycerin (USP) which is a model that behaves like the slush prepared in accordance with the present invention. The contact angle between the liquid drop and the belt was measured from a back-lit 0.7-3-fold magnified photograph (Contact Angle System OCA, Data physics Instruments, GmbH Raiffeisenstraße, Filderstadt, Germany) by using a protractor (Acme United Corporation. Fairfield, Conn.). The left and right side of each of two droplets were photographed, measured and averaged.

| Belt # | contact angle of glycerin drop |
|---|---|
| 1 | 103 ± 1° |
| 2 | 68 ± 1° |
| 3 | 94 ± 1° |
| 4 | 108 ± 7° |
| 5 | 143 ± 7° |

The contact angle of xylitol pieces formed by depositing on different belt materials were backlit and photographed. The contact angle was determined as the angle of its side at the point it intersects its flat bottom. Four pieces were examined measuring the contact angle on each of four points approximately at points 90° removed from each other around the edge of piece.

| Belt # | contact angle of glycerin drop |
|---|---|
| 1 | 90 ± 3° |
| 2 | 78 ± 7° |
| 3 | 106 ± 8° |
| 4 | 103 ± 6° |
| 5 | 156 ± 15° |

From this, depositing xylitol slush directly on a belt produces a desirable rounded candy piece when the belt on which it is deposited has a contact angle about 110°.

Example 10

The drop-deposited xylitol piece of Example 2, deposited onto belt #5 of Example 9, was examined using Contact Angle System OCA, in which the pieces were held on edge using formed aluminum foil and sidelit using fiber-optic directed light (KL1500-Electronic, Schott North America, Inc., Elmsford, N.Y.). The images were then measured against the distance of 1-mm also imaged under the same conditions.

Figure 4:
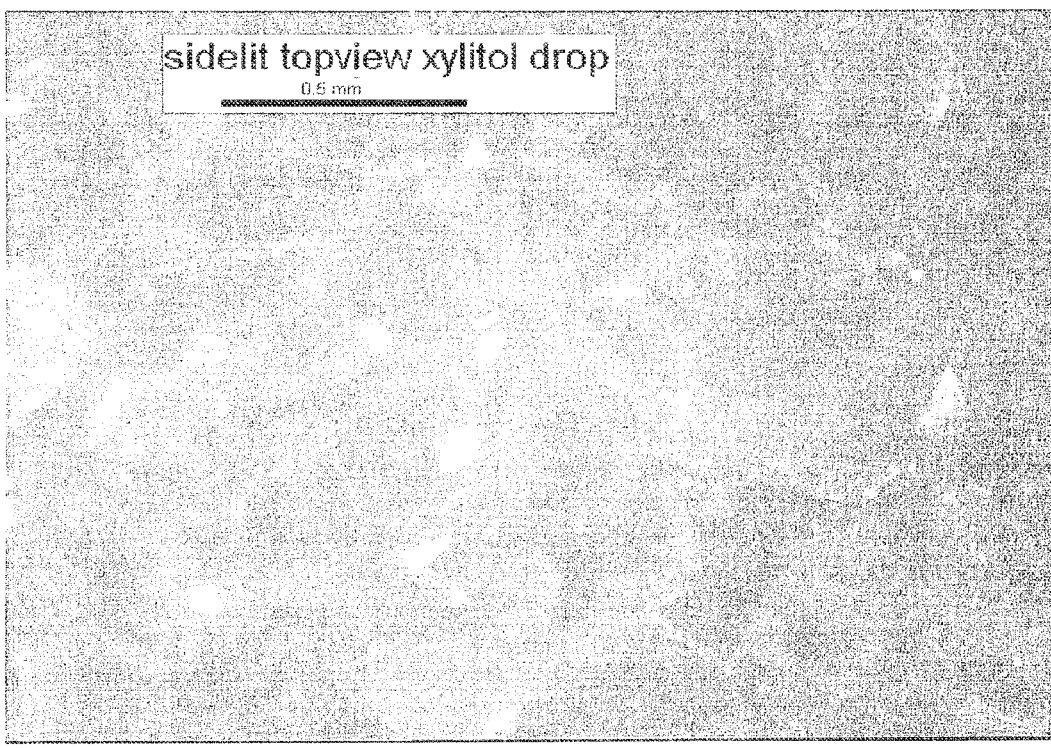
FIG. 4 is a microscopic image magnified 400× of a drop of the xylitol composition in Example 10.

The crystal sizes were identified as domains of uniform light intensity bounded completely by lighter colored lines of irregular shape. The longest and shortest dimensions were measured and recorded. A picture of the crystals is depicted in FIG. 4.

Results: Nine crystals were evident and had the following dimensions in micrometers. 400×180, 280×280, 420×320, 580×320, 210×210, 210×210, 350×140, 170×140.

Example 11

The drop-deposited xylitol piece of Example 2 was imaged along its top essentially looking along the top almost parallel to surface so as to image the peaks and valleys. The same equipment was used as in Example 10. The height of the elevations were estimated from the photomicrographs produced, which is depicted in FIG. 5.

Figure 5:
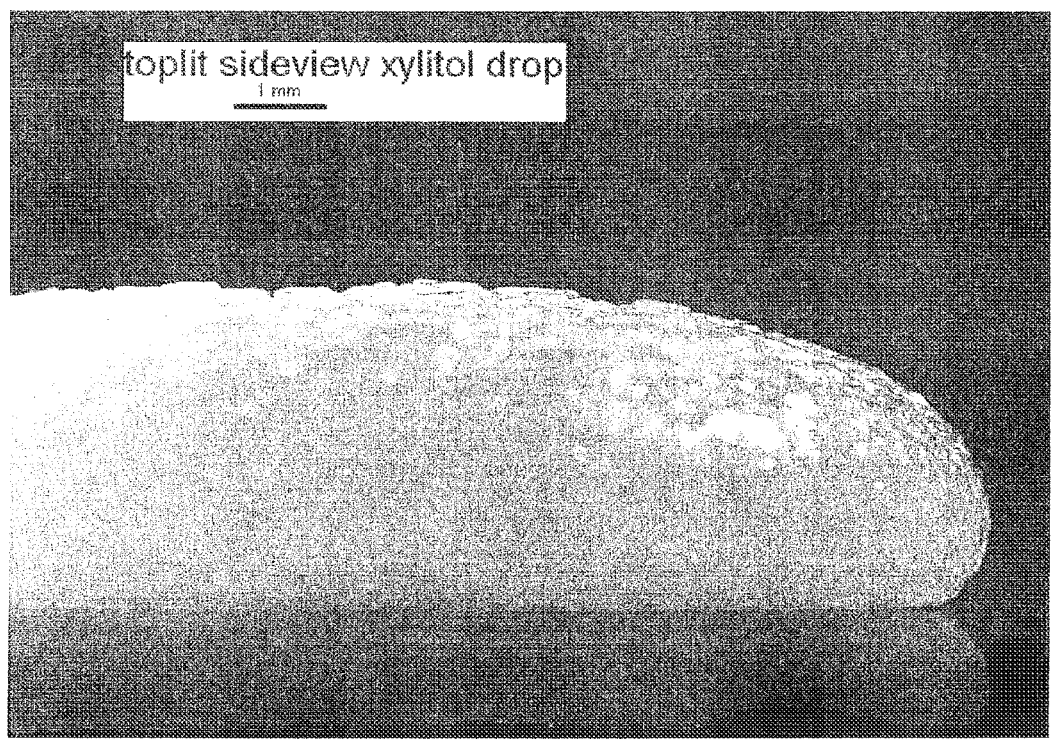
FIG. 5 is a photomicrograph of the drop deposited xylitol composition from Example 11.

As shown in FIG. 5 along the top, peak to trough was observed to be less than 300 micrometers, while along the side near the belt, it was observed to be less than 50 micrometers.

Example 12

Granular xylitol (66.3% w/w), aspirin (32.5% w/w) powdered cooling compound WS23(N, 2,3-trimethyl-2-(1-methylethyl) butanamide (0.2% w/w) and granular peppermint flavor (1% w/w) were dry blended in a small batch mixer at ambient temperature of about 65 F-75 F. The dry blending continued until a homogenous mixture was obtained. The dry blend mixture was then fed into a water jacketed cooled hopper which feeds the product into a single screw extruder (Wayne, Totowa, N.J. having a 24:1 L/D ratio, 1 inch diameter screw in a 3:1 compression ratio). The extruder has five temperature controlled zones through which the mixture passed. The temperature in the various zones was set at about the melting point of xylitol, and the discharge of the extruder was at 198 F. The mass was solidified in a mold in the shape of a mold within 2-3 minutes after being placed into a mold that was then exposed to ambient air temperature. The product produced was a soft hard candy in the shape of a mold that was easily broken by biting into it.

Example 13

The process of Example 12 was repeated, except the amount of aspirin present was 8% (w/w) and the amount of xylitol was 91.8% (w/w).

The above preferred embodiments and examples are given to illustrate the scope and spirit of the present invention. The embodiments and the examples described herein will make apparent to those skilled in the art other embodiment and examples. These other embodiments and examples are within the contemplation of the present invention.

What is claimed is:

1. A solid homogenous non-compressible comestible product comprising from about 60% up to and including 100% solid xylitol, by weight and substantially free of any other sugar alcohol and substantially free of monosaccharides and disaccharides and maltodextrin having a DE of less than 20, and having a moisture content of less than about 1% by weight, said product, if formed into a yertz shape and having a base width of 8.20 mm and a length of about 13.26 mm, a height of 8.71 mm, a 10% angle between the vertical and a side thereof and having 0.25 mm fillet and weighing about 0.75 grams, exhibits a piece break pressure of less than about 110 MPa and a dissolution rate in water from about 200 to about 400 seconds.

2. The comestible product according to claim 1 comprised of at least about 70% by weight xylitol.

3. The comestible product according to claim 2 comprised of at least about 80% by weight xylitol.

4. The comestible product according to claim 3 comprised of at least about 95% by weight xylitol.

5. The comestible product according to claim 1 comprising one or more additional ingredients selected from the flavorants, coloring agents, cooling agents, food additives and food grade processing agents.

6. The comestible product according to claim 1 wherein sodium bicarbonate is additionally present.

7. The comestible product according to claim 4 wherein sodium bicarbonate is present.

8. The comestible product according to claim 1 additionally comprising a pharmaceutical.

9. The comestible product according to claim 8 wherein the pharmaceutical is an analgesic.

10. The comestible product according to claim 9 wherein the analgesic is aspirin.

11. The comestible product according to claim 8 wherein the pharmaceutical is present in therapeutically effective amounts and up to about 40% by weight.

12. The comestible product according to claim 11 where the pharmaceutical is present in amounts ranging from about 0.01% to about 40% by weight.

13. The comestible product according to claim 1 in the form of a disc.

14. A solid homogenous non-compressible comestible product comprising from about 60% up to and including 100% solid xylitol by weight and substantially free of any other sugar alcohol and substantially free of monosaccharides and disaccharides and maltodextrin having a dextrose equivalent (DE) of less than 20%, and having a moisture content of less than about 1% by weight, said product, if formed into a yertz shape configured as a vertical elliptical cylinder that is wider at a first end of the cylinder than at an opposite second end of the cylinder, exhibits a piece break pressure of less than about 110 MPa.

15. The comestible product according to claim 14, wherein the first end of the elliptical cylinder is formed as an ellipse having a width of about 8.2 mm and a length of about 13.3 mm, the elliptical cylinder has a height of about 8.7 mm, the elliptical cylinder has sides extending from the first end to the second end, and at least portions of the sides are angled at about 10% from vertical.

16. The comestible product according to claim 14 in the form of a disc.

17. The comestible product according to claim 14, wherein the product, when formed into said yertz shape, exhibits a dissolution rate in water from about 200 to about 400 seconds.

18. A solid homogenous non-compressible comestible product comprising from about 60% up to and including 100% solid xylitol by weight and substantially free of any other sugar alcohol and substantially free of monosaccharides and disaccharides and maltodextrin having a dextrose equivalent (DE) of less than 20%, and having a moisture content of less than about 1% by weight, said product, if formed into a yertz shape configured as a vertical elliptical cylinder that is wider at a first end of the cylinder than at an opposite second end of the cylinder, exhibits a dissolution rate in water from about 200 to about 400 seconds.

19. The comestible product according to claim 14, wherein the first end of the elliptical cylinder is formed as an ellipse having a width of about 8.2 mm and a length of about 13.3 mm, the elliptical cylinder has a height of about 8.7 mm, the elliptical cylinder has sides extending from the first end to the second end, and at least portions of the sides are angled at about 10% from vertical.

20. The comestible product according to claim 14 in the form of a disc.

* * * * *